United States Patent [19]
Panzera et al.

[11] Patent Number: 6,030,209
[45] Date of Patent: Feb. 29, 2000

[54] METHOD FOR ACCURATELY PREPARING THE COLOR OF A DENTAL RESTORATION

[75] Inventors: Carlino Panzera, Belle Mead; Paul Panzera, Mount Holly; Lisa M. Kaiser, Monmouth Junction; Jana N. Pruden, Belle Mead, all of N.J.

[73] Assignee: Jeneric/Pentron Incorporated, Wallingford, Conn.

[21] Appl. No.: 09/173,227

[22] Filed: Oct. 15, 1998

Related U.S. Application Data

[60] Provisional application No. 60/062,369, Oct. 15, 1997, and provisional application No. 60/062,343, Oct. 15, 1997.

[51] Int. Cl.$^7$ .............................. A61C 1/02; A61C 13/08
[52] U.S. Cl. ......................................... 433/26; 433/203.1
[58] Field of Search ................................... 433/26, 202.1, 433/203.1, 208, 212.1, 218, 223

[56] References Cited

U.S. PATENT DOCUMENTS

| | | |
|---|---|---|
| 3,507,042 | 4/1970 | Hana . |
| 3,932,938 | 1/1976 | Mackta . |
| 3,964,167 | 6/1976 | Yerkes . |
| 3,992,781 | 11/1976 | Sturdivant . |
| 4,115,922 | 9/1978 | Alderman . |
| 4,207,678 | 6/1980 | Jeannette . |
| 4,382,784 | 5/1983 | Freller . |
| 4,433,959 | 2/1984 | Faunce . |
| 4,654,794 | 3/1987 | O'Brien . |
| 4,657,399 | 4/1987 | Hall . |
| 4,715,813 | 12/1987 | Mühlbauer . |
| 4,744,378 | 5/1988 | Bostic . |
| 4,802,850 | 2/1989 | Boon . |
| 4,810,193 | 3/1989 | Wieder . |
| 4,828,117 | 5/1989 | Panzera et al. . |
| 4,836,674 | 6/1989 | Lequime et al. . |
| 4,919,617 | 4/1990 | Antons et al. . |
| 4,978,296 | 12/1990 | Antons et al. . |
| 5,004,417 | 4/1991 | Giaramita . |
| 5,055,040 | 10/1991 | Clar . |
| 5,078,598 | 1/1992 | Neisse . |
| 5,114,340 | 5/1992 | Hahn . |
| 5,149,267 | 9/1992 | Longhini et al. . |

(List continued on next page.)

FOREIGN PATENT DOCUMENTS

| | | |
|---|---|---|
| 0 777 113 A1 | 5/1987 | European Pat. Off. . |
| 2 669 526 | 5/1992 | France . |

OTHER PUBLICATIONS

Quintessence Publishing Co., Inc. "Dental Ceramics Proceedings of the First International Symposium on Ceramics", 1983, pp. 64–70.

Dentsply/York Division, *"The Trubyte Primer"*, 1983, pp. 22–39.

Paul A. Lemire, C.D.T., *"Color in Dentistry"*, 1975, pp. 74–79.

J. M. Ney Co., *"Supplement to Color in Dentistry"*, 1975 pp. 2–19.

Vita, Vitapan 3D–Master: *"The entire world of tooth shades"*, 4 pgs.

*Primary Examiner*—Nicholas D. Lucchesi
*Attorney, Agent, or Firm*—Cantor Colburn LLP

[57] ABSTRACT

The present invention relates to a method for preparing the color of a dental restoration using a spectrophotometer and a unique color system for porcelain dental restorations which enables a dentist or technician to manipulate the various color components of the porcelain, hue, chroma, value, and translucency, independently. Color component deltas between consecutive colors in the powder sets are equidistant, with the difference in values being linear in color space. This enables simplified, exact matching of a specified color component value. The method comprises illuminating an abutting tooth with light, gathering reflected light, converting the gathered light to analog signals, correct for ambient light interference, translucency effects (if necessary) and varying illumination, using the result to obtain accurate color component values, and employing those values to chose and, where necessary, mix the appropriate powers to obtain the correct color porcelain for the desired dental restoration.

25 Claims, 4 Drawing Sheets

U.S. PATENT DOCUMENTS

| | | |
|---|---|---|
| 5,240,414 | 8/1993 | Thompson . |
| 5,257,931 | 11/1993 | Pozzi . |
| 5,261,815 | 11/1993 | Pozzi . |
| 5,308,243 | 5/1994 | Emmons ............................... 433/203.1 |
| 5,346,397 | 9/1994 | Brainman . |
| 5,364,267 | 11/1994 | Fischer . |
| 5,428,450 | 6/1995 | Vieillefosse et al. . |
| 5,464,348 | 11/1995 | Fischer et al. . |
| 5,482,459 | 1/1996 | Yarovesky et al. . |
| 5,482,464 | 1/1996 | Shimosawa et al. . |
| 5,482,732 | 1/1996 | Kramer . |
| 5,498,157 | 3/1996 | Hall . |
| 5,529,492 | 6/1996 | Yarovesky et al. . |
| 5,588,834 | 12/1996 | Resk et al. . |
| 5,624,262 | 4/1997 | Yarovesky et al. . |
| 5,639,235 | 6/1997 | Lapointe et al. . |
| 5,662,472 | 9/1997 | Grutzner . |
| 5,685,717 | 11/1997 | Kramer . |
| 5,690,486 | 11/1997 | Zigelbaum . |
| 5,718,585 | 2/1998 | Dehoff ............................ 433/203.1 X |
| 5,759,030 | 6/1998 | Jung et al. . |
| 5,766,006 | 6/1998 | Murljacic . |
| 5,800,164 | 9/1998 | Pfau . |
| 5,906,490 | 5/1999 | Primus et al. ....................... 433/203.1 |
| B1 3,986,261 | 7/1990 | Faunce . |
| B1 4,650,418 | 12/1989 | Blair et al. . |

METHOD FOR ACCURATELY PREPARING THE COLOR OF A DENTAL RESTORATION

CROSS-REFERENCE TO RELATED APPLICATIONS

This application claims priority to U.S. Provisional Application Ser. No. 60/062,369, filed Oct. 15, 1997, and to U.S. Provisional Application No. 60/062,343, filed Oct. 15, 1997, which are incorporated herein by reference.

BACKGROUND OF THE INVENTION

1. Field of the Invention

This invention generally relates to dental porcelain restorations and methods of manufacture thereof. In particular, this invention relates to a color dental porcelain system and a method of use of the system for accurately matching the color of a porcelain restoration to a patient's natural tooth color.

2. Brief Description of the Related Art

In the restoration of a tooth or a set of teeth, the tooth color must be correctly selected. A tooth restoration should not only fit harmoniously into the arc of the teeth but it should also be adapted to the individual conditions of the adjacent teeth and the entire set of teeth in its course of colors.

Tooth color is affected by a number of factors. The inherent color of the restoration is important, as well as the spectral composition of the particular light source with which the restoration is illuminated. The natural tooth is not opaque, but more or less translucent on its surface; for this reason, the transparencies of the enamel and of the dentin need to be taken into consideration. Light reflections result in bright spots and bright lines, so even the surface nature of the replacement tooth must agree with the surface of the adjacent teeth. It has long been known in the dental profession that the good aesthetics of dental prostheses are to a significant degree determined by the hue, the chroma, and the value of the visible exposed portions of the dental restoration. Translucency is also an important color parameter.

As used herein hue is a color or the name of a color, for example, blue, red, orange, violet, green, and so forth. A hue may be a primary color or the result of a combination of colors, for example, greenish-blue or orangish-yellow. The hues of primary interest in dental restorations are red and yellow. Chroma as used herein refers to the strength, intensity, or amount of saturation of the hue. Value as used herein refers to the brightness of a color in the range of white to black. Any point in between white and black will comprise a certain intensity of gray. For example, a darker gray color will have a low value, while a lighter gray will have a higher value. Value is one of the more important factors in proper tooth matching, as a tooth of high value is generally bright and vital, whereas a tooth with a low value has a non-vital, gray appearance. Translucency as used herein is the quality of transmitting and diffusing light, which gives a perception of depth, and is expressed in the range from transparent to opaque.

The parameters of hue, value, and chroma are often presented in the form of a three-dimensional array having a uniform color scale. One commonly-used system employs the CIE (Commission Internationale de l'Eclairage [International Commission of Illumination]) $L^*a^*b$ conventions, which represents colors in a three-dimensional Cartesian co-ordinate system. The vertical axis represents luminance or lightness "L", which is equivalent to value. The horizontal co-ordinates represent chromaticity, and are designated "a" (positive representing red and negative representing green) and "b" (positive representing yellow and negative representing blue). Thus, the positive and negative portions of the horizontal axes represent opposed colors of increasing chroma moving way from the axes. Hue is calculated mathematically as $\tan^{-1}(b^*/a^*)$ Chroma is calculated as $([a^{*2}+b^{*2}])^{1/2}$. A variant of this co-ordinate system expresses the rectangular co-ordinates "a" and "b" as polar coordinates "C" and "h", where "C" is the magnitude component representing chroma and "h" is the angular component representing hue. Value or lightness if plotted on the z-axis through the sphere.

Hue, chroma, value, and translucency define the color components found individually in varying degrees and cooperatively in varying ratios in every tooth color. However, a proper interpretation and accurate communication of the varying degrees and ratios of these parameters is difficult. A common practice in the dental arts in the selection of colors is to employ a dental shade guide to assist in the matching of a patient's natural tooth color. A typical prior art shade guide includes an elongated, linear holder containing a plurality of specimens. Each of the specimens is comprised of a sample tooth and a support member for attaching the sample tooth to the holder. Each sample tooth is provided with a predetermined shade value, chroma, and hue for matching with the patient's natural teeth.

The dentist places the shade guide teeth in front of the patient's natural teeth to select a shade most closely approximating the coloring of the patient's natural teeth. Then the dentist, often together with the patient, typically selects a hue and shade progression according to the age of the patient. After the best color match has been selected, the dentist communicates this coloring to the dental ceramist, who then constructs the dental restoration by selecting appropriate porcelain powders. The selection of the porcelain powders is usually dictated by the letter and number code that is communicated to the dental ceramist.

One drawback with existing systems is the trial-and-error nature of trying to match the dental restoration color to the patient's teeth. While the colors of teeth appear to range from a light almost white-tan to a light brown, the colors involved may actually contain a small amount of nearly any color of the visual spectrum. Even a slight variation in color will become apparent when the dental restoration is positioned closely adjacent to natural teeth. Teeth appear to be different colors under different illumination systems (e.g., natural vs. fluorescent light) and light levels, which further complicates shade selection. In addition, the color of an individual tooth is not evenly and uniformly distributed. The color, brightness, and transparency decrease from the cutting edge or the masticatory surface of a tooth to the dental neck. The enamel exhibits a whitish-bluish color and the dentin exhibits a yellowish to brownish color tones. The dental neck and the root element are likewise of a yellowish-brownish color but usually are darker than the corresponding dentin. The canines are usually darker than the other teeth.

Existing color shade guides and the porcelain systems used with them typically do not allow a dentist or technician to independently increase or decrease each one of the color components (e.g., translucency) without affecting the other three color components (e.g. hue, chroma, or value) for each of the color parameters. A shade guide system presently in widespread use is the guide manufactured by Vita Zahnfabrik under the trade name Vita Lumen® Vacuum Shade Guide. As shown in FIG. 1, the shades are somewhat arbitrarily distributed within color space.

Attempts have been made to allow greater flexibility in shade matching, but none is at present entirely satisfactory. For example, U.S. Pat. No. 4,207,678 to Jeannette discloses a dental shade guide system having a plurality of primary shade guides having a specific chroma percentage, and each primary shade guide having a corresponding plurality of secondary shade guides such that each of the secondary shade guides has a decreased chroma percentage. The decreased chroma percentage in each secondary shade guide is accomplished by mixing the primary shade guide formula in varying amounts with a gray or white modifier. A primary shade guide is first selected and then a color selection is made from the corresponding secondary shade guide.

U.S. Pat. No. 5,240,414 to Thompson discloses a method of shade selection which uses a plurality of shade tabs to simulate color reproduction and/or tooth shade. An opaque porcelain tab having preselected characteristics is first selected; then, a dentin porcelain tab of preselected characteristic is selected and interfitted upon the opaque tab; next, an enamel tab of preselected characteristics is selected and interfitted upon the dentin tab. U.S. Pat. No. 3,964,167 to Yerkes discloses a disposable tooth shade guide having an artificial tooth of a predetermined shade mounted on a holder with a cap or covering detachably mounted over the artificial tooth. The cap/cover is colored a predetermined shade whereby when it is mounted on the artificial tooth, it alters the basic color of the artificial tooth to produce a variation in shade. Each of these above-described methods is limited in that only one of the four color parameters is addressed in determining proper tooth color.

In contrast, U.S. Pat. No. 5,529,492 to Yarovesky et al. addresses the problem that conventional shade guides do not permit the dentist to inform the laboratory regarding the characteristics to be incorporated into the prosthesis, for example differences between the neck portion and the incisal portion of the tooth, or cracks or other localized discolorations. This patent discloses an anterior tooth characterization guide which includes several sets of anterior tooth samples which have differing, independently selectable color characteristics including the dentin color, the incisal color, the body:incisal relation, the dentin structure and translucent effect, characterizations, and amount of white stain. The guide is utilized to first select a dentin color (keeping incisal color constant), the incisal color (keeping dentin color and blend constant), and the body to incisal relation (keeping dentin color constant). The dentin structure and translucent effect are then determined holding the dentin color constant, additional characterization features including cracking, spotting, and hallow are then selected holding dentin color constant, and finally, the amount of white stain is determined holding the dentin, enamel and blend constant. While this method holds various aspects of tooth coloration constant while varying others to enable a choice of a particular prosthesis color and characteristic, it is a multi-step, time-consuming process. It furthermore fails to address the formation of an appropriate prosthesis and does not allow independent variation among hue, value, and chroma for each of the tooth parts.

This deficiency is at least partially remedied by the systems disclosed U.S. Pat. Nos. 5,498,157 and 4,657,399 to Hall, which are incorporated herein by reference. Hall discloses dental color systems comprising arrayed color samples which coincide with an evenly-spaced, corresponding location on a CIE L*a*b color co-ordinate system. As disclosed by Hall, a set of dental shade guides is constructed based first on selection of two or more evenly spaced value or lightness levels. For each value or lightness level, a set of seven shades is provided having various a, b (hue and chroma) values. The a, b values within the set correspond to the intersection points of a grid as laid out on the a, b axes. The size, placement, and number of intersections of grid is preferably selected so as to correspond to the majority (>95%) of the range of hue and chroma values of human teeth as determined by Hall. The distance between any two adjacent colors along the b-axis is therefore about 5 units, while the difference between adjacent colors along the a-axis is about 2.5 units. Each grid preferably has a central color, which is offset from the central color in the adjacent level by 2–4 degrees of hue towards the red for each 4–6 unit decrease in luminance.

Although Hall represents an advance over prior art systems for judging and communicating tooth color, it still has a number of drawbacks and disadvantages. One of these is the necessity for the arbitrary selection of a set lightness, hue, and value parameters for the manufacture of the shade guide and of the porcelain. While Hall has systematized selection of these parameters to some extent, the particular shades provided to the practitioner still remains arbitrary, and will not match all tooth colors. The practitioner is forced to estimate the approximate distance between two adjacent colors in these instances.

Another drawback to the Hall system is that there is no provision for translucency. Translucency has been particularly difficult to reproduce accurately. Natural teeth, as well as properly made dental restorations, are to some extent translucent so that the color of the back of a tooth, particularly the back of the lower part of the incisal portion of a tooth may be as important as the color of the front or normally exposed portion of a tooth. Within a tooth, there may be regions of varying translucency. Furthermore, the translucency of teeth increases as people age. U.S. Pat. No. 5,114,340 to Hahn discloses a platelet color specimen having at least one lateral edge concavely curved towards the center region, wherein the specimen is on the order of a width of a tooth. The platelet color specimen exhibits only a single hue having varying transparency corresponding to enamel, dentin, or dental neck. As with other color guides, however, the range of colors and other variables is limited.

In addition to the above described drawbacks, the color systems of the prior art do not provide accurate color matching because of human error, i.e., the doctor or fabricating technician may misread the color number on the shade guide or the shade guide manufacturer may erroneously identify the shade of one or more specimens in the shade guide. There may be inconsistency between the laboratory and dentist in the type of shade guide. The tooth manufacturer may slightly change the shades of teeth or tooth powder in its production batches because of changes, which frequently depend upon availability, of one or more ingredients.

Another source of error arises because shade guides age, which changes the apparent colors of the guide. For example, the color intensity is reduced and colors tend to lighten or fade with time. This is particularly true where the shade guide is overexposed to sunlight, frequently disinfected, or sterilized, resulting in a change in the original tones. Finally, it is noteworthy that the tooth portions of shade guides are often manufactured from acrylic or similar materials, rather than porcelain. The differences between the shades achievable in plastics and those of porcelain provide further subtle inaccuracies. The occurrence of any of these events will result in an inaccurate matching of artificial teeth shade with the shade of natural teeth because the technician normally does not have access to the patient and was not present when the dentist made the initial shade selection.

Accordingly, there remains a need in the dentistry field for a color system for porcelain dental restorations in which the color of the porcelain restoration is accurately measured and communicated to the laboratory, and porcelain powders can be mixed in accordance with the reported values to achieve a restoration matched to the color of the patient's natural teeth. In particular, there remains a need for a system which the color components (hue, chroma, value, and translucency) of a patient's tooth are independently taken into account when selecting the proper color of a porcelain dental restoration, and are not limited by an arbitrary selection of colors within the relevant color space.

SUMMARY OF THE INVENTION

The above-described and other problems and deficiencies of the prior art are overcome or alleviated by the present invention comprising a color system for porcelain dental restorations and method of use. The present system utilizes colorimetric data from a spectrophotometer device. Preferably, the device measures and provides colorimetric data regarding hue, chroma, value, and translucency for each of the incisal, middle, and cervical regions of the tooth. This colorimetric data is then converted via an algorithm to a recipe that the dentist or dental technician follows in constructing the restoration. The color system further comprises a system of porcelains and shade guides coded to these porcelains which will have colors that are selected on a polar co-ordinate system so as to have a regularly space, linear relationship in color space in all dimensions. Importantly, the present invention provides a porcelain system which allows a dentist or technician to independently alter one color component while not affecting the other three color components. By being able to independently alter one color component of the system, the dentist or technician can prepare a dental restoration with a color that closely matches the color of a patient's tooth. Because the relationships of the various shades to one another are linear, shades falling out of the predetermined shades are easily calculated and manufactured by the dentist or technician from the porcelain powders provided.

DETAILED DESCRIPTION OF THE INVENTION

Figure 2:
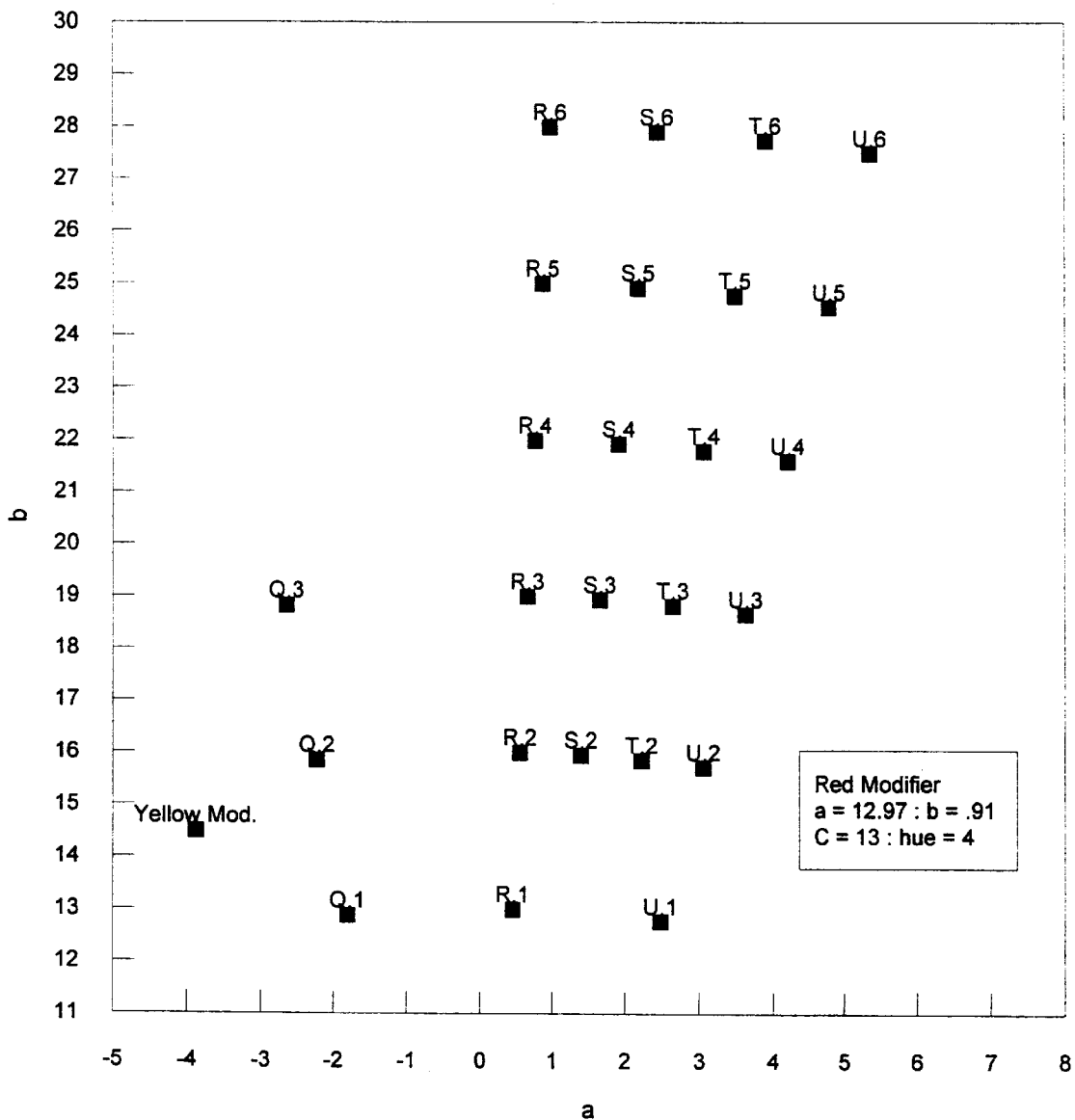
FIG. 2 is a graph showing the distribution of 24 shades of porcelain in accordance with one embodiment of the present invention.
Figure 3:
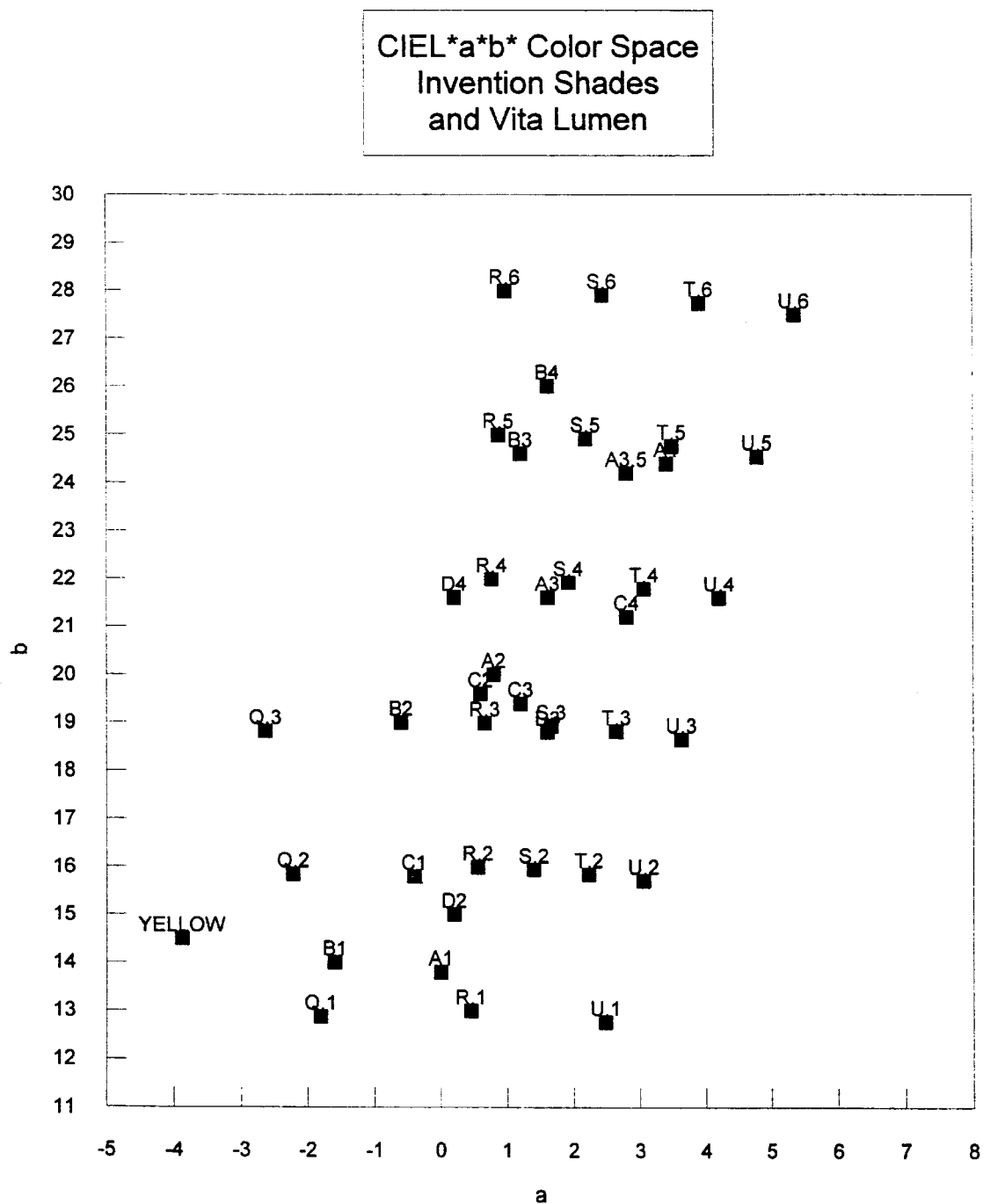
FIG. 3 is an overlay of the graphs of FIG. 1 and FIG. 2 showing the congruence of the shades of the Vita system and the system in accordance with an embodiment of the present invention.

The present invention is directed to color dental system for accurately matching the color of a porcelain restoration to a patient's natural tooth color. In accordance with the present invention, the color of the patient's tooth or teeth is determined spectrophotometrically. This data is then used to select porcelain powders having colors that are regularly spaced in color space as shown in FIG. 2, wherein the porcelains are mixed to provide a restoration having a color corresponding to the reported color. Since relationships of the colors to one another are equidistant when plotted in a polar co-ordinate color space, mixtures of powders for tooth shades not corresponding to the predetermined shades are readily calculated. This system encompasses all the shades which exist in the previous Vita system as shown in FIG. 3, but in a much more organized combination. The porcelains allow the dentist or technician to:

1. increase or decrease translucency without affecting hue, chroma or value.
2. increase or decrease value without affecting translucency, hue or chroma.
3. increase or decrease chroma without affecting value, hue or translucency.
4. change hue without affecting value, chroma or translucency.

In accordance with the present invention, the color system is designed to utilize a spectrophotometer device and to enable manufacture of a dental restoration based on colorimetric data from the same. In particular, the method of the present invention comprises using a spectrophotometer to measure and arithmetically evaluate colorimetric information, converting the information to a format intelligible to the dentist or technician via an algorithmic expression, and providing a system of porcelains corresponding to the format provided to the dentist or technician.

A number of spectrophotometric devices have been described in the art, and may be used to provide colorimetric data, for example U.S. Pat. No. 4,654,794 to O'Brien; U.S. Pat. No. 5,428,450 to Viellefosse et al; U.S. Pat. No. 4,836,674 to Lequime et al.; U.S. Pat. No. 5,690,486 to Ziegelbaum et al; U.S. Pat. No. 5,759,030 to Jung et al; and U.S. Pat. No. 5,766,006 to Murljacic, all of which are incorporated by reference herein in their entirety. The tristimulus values, x, y, and Z obtained by the spectrophotometer are used to calculate the CIE coordinates $L^*a^*b$. From the color coordinates, and calibration data for the pigments, formulas are made that have the color coordinates desired. The principles underlying the utilization of CIE tristumulus values and their calculation from the spectral response of a given color are known to those skilled in the art of color analysis. For instance, see Billmeyer and Saltzman, PRINCIPLES OF COLOR TECHNOLOGY, Second Edition, John Wiley & Sons, 1981, especially pages 44–46, 80–83, and 174, and Judd and Wyszecki, COLOR IN BUSINESS & SCIENCE AND INDUSTRY, Third Edition, John Wiley & Sons, 1975, especially pages 139–169, for discussions of the methods used to calculate CIE tristimulus values.

Briefly, the CIE tristimulus values are obtained from the spectrophotometric data by multiplying, wavelength by wavelength, the spectral reflectance of the sample (R), the relative spectral power of the illuminant, and the values of the respective CIE standard observer functions ($P_{x1}P_{y1}P_z$). These products are then added up for all the wavelengths in the visible region of the spectrum. Tables are available that give the products of the CIE standard observer functions and the spectral power for various CIE illuminants (e.g., daylight, incandescent, and fluorescent) for each wavelength. These tables are used to calculate the tristumulus values for standard daylight, incandescent, and fluorescent light sources for the sample under evaluation.

Thus, calorimetric information of at least one tooth abutting the tooth to be replaced (or missing tooth) is obtained as follows. The probe head of a spectrophotometer contacts a reference object and a measurement is taken by illuminating a first spot, gathering reflected light, sending the gathered light to a spectrometer where it is converted into its spectral components and converted into first analog signals, and subsequently illuminating a second spot, gathering second reflected light, sending the second gathered light to a spectrometer where it is converted into its spectral components and converted into second analog signals, digitizing and storing the first and second analog signals. The abutting tooth is measured in the same manner as described with relation to the reference tooth to obtain abutting tooth analog signals. Another measurement of the abutting tooth is taken by contacting the abutting tooth with the probe head, gathering light reflected from the tooth without illuminating the tooth (to obtain an ambient reading adjustment), sending the gathered light to a spectrometer where it is converted into its spectral components and ambient analog signals, digitizing and storing the ambient analog signals. The correct remission spectrum is calculated, removing the ambient influence from the abutting tooth analog signals, correcting varying luminance utilizing the reference values, and correcting for light loss due to translucency to obtain adjusted remission data. The corrected remission data is obtained using the reference object remission data, and the corrected remission data is used to evaluate correct colorimetric information.

A particularly preferred spectrophotometer is a hand-held spectrophotometer disclosed in European Patent Publication No. 0-777-113 A1, which is herein incorporated by reference in its entirety. This device is known as a Pikkio spectrophotometer, manufactured by MHT, Optic Research, Niederhasli, Switzerland. The device is particularly advantageous in that it has a 1 mm spot size and is therefore capable of providing separate measurements of the incisal, middle, and cervical regions of a tooth. The device is further advantageous in that it can provide data regarding each of the four colorimetric parameters of hue, chroma, value, and translucency.

Accordingly, at least two measurements with differing illumination areas and/or differing measuring areas are performed, in which a correction value is calculated on the basis of reference value measured on reference objects, by means of which the measurement values are corrected to determine the color stimulus specification under consideration of the translucency thereof. The color stimulus specification of a translucent object under test can be determined with much higher accuracy than it was possible up to now. Difficulties with respect to ambient light are solved by taking the influence of the ambient light into account by the step of performing a further measurement value during calculating the final color stimulus specification.

In a first step, reference data are gathered, whereby a measurement is performed with an opaque reference object as an object under test. During the measurement, two lamps are activated one after the other, such that the reference object is illuminated firstly with the first spot having a smaller diameter and thereafter with the second spot having a greater diameter. Via a lens and a light conductor coupled thereto, the reflected light is picked up and sent to the spectrophotometer, where, in a manner known per se, it is divided into its spectral components and converted into corresponding analog signals. These analog signals are digitized in an A/D-converter and stored in the memory module of the data processing unit. In this way, two reference measurement values are created, i.e. a first reference value obtained from the measurement with the smaller spot and a second reference value obtained from the measurement with the greater spot.

After these reference measurements have been made, the real measurement of the color stimulus specification of an object M to be tested can be done, i.e. any number of measurements on a plurality of different objects to be tested can be done. As soon as the probe head has approached the object under test M, the measurement is initiated. Thereby, three consecutive measurements are performed. The first and seconds measurements correspond to the ones performed on the reference object, inasmuch as the object under test is illuminated with two differently sized light spots and the measured values are evaluated and stored as has been described herein before. In this way, a third measurement is done without illuminating the object under test M. In this was, a fifth measurement value e is obtained which is proportional of the ambient illumination.

On the basis of these five measurements, which all were spectral measurements, i.e. functions of the wave length f $(\lambda)$m the correct remission spectrum R $(\lambda)$ can be calculated, i.e. that remission spectrum R $(\lambda)$, which one would have obtained if the object under test had been illuminated by means of a light spot with infinite size. On the basis of the remission data R $(\lambda)$, the correct color stimulus specification of the object under test can be evaluated; the method therefor is well known to any person skilled in the art.

The remission data of the reference object have previously been measured, for example by the manufacturer of the apparatus during the calibration, with the help of an arbitrary remission spectrophotometer, and have been stored in a memory module of the apparatus. Moreover, the function f (d2, c2) has previously been determined, e.g. by the manufacturer of the apparatus, by storing the measurement values of many different reference objects with varying remission data and varying translucency in a memory module of the apparatus. In practice, such reference objects are measured first with a light spot having a diameter d2, and finally with a light spot having a diameter as large as possible, and the measurement values are stored in the memory module. The measurement value obtained during the measurement with the third large light spot corresponds to the function value f(d2,c2). The particular function values can, thereafter, stored in a memory module of the apparatus in the form of a table.

In the case of measuring the color of teeth and of determining of the correct composition of a denture, respectively, the previously mentioned reference dentures are measured with the apparatus according to the invention in order to be in a position to select the composition with matches best. This can be done either by the manufacturer of the apparatus of by the operator of the apparatus himself. The color stimulus specifications of the reference dentures, then, are stored in a memory module of the apparatus. After having measured a natural tooth, the apparatus is easily in a position to select that reference denture out of a plurality of reference dentures, whose color stimulus specification matches the color stimulus specification of the measured natural tooth best, i.e. to select that reference denture, which has the least color difference compared with the natural tooth. The calculation of the color difference, again, is disclosed in the prior art and well known to a skilled person.

Colorimetric information obtained from a spectrophotometer is particularly adapted for use with the color system of the present invention, which provides means for independently varying each of the four color parameters to obtain an exact or very close color match. This is illustrated by plotting the porcelain powder colors on a polar co-ordinate system, which shows the colors to have a regularly spaced, linear relationship in color space. Because the relationships of the various shades to one another is linear, the shades falling out of the predetermined shades can easily be calculated.

Importantly, the present invention provides a porcelain system which will allow a dentist or technician to independently alter one color component while not affecting the other three color components. For example, the value component of the porcelain mixture may be increased or decreased without affecting the hue, chroma, or translucency. Thus, by being able to independently alter one color component of the system, the dentist or technician can prepare a dental restoration whose color closely matches the color of a patient's tooth.

Accordingly, the present invention provides porcelain powders in which all hue shades are equi-distant in relationship in a polar co-ordinate system. For all hue shades which can be found on the same angle as represented graphically in FIG. 2, all hues have the same value and are provided at the same translucency. Hue shades farther from the ordinate on a given hue angle have increased intensity or chroma. These can be combined on the same hue angle to achieve a chroma in-between two hue shades. Likewise, the dentist or technician can achieve a match to a tooth having a hue and chroma falling between two hue angles by combining two porcelains having hue and chroma which bracket the shade.

In a preferred embodiment, porcelain powders having the 24 hue shades presented graphically in FIG. 2 are provided, wherein L=60, and translucency is provided at a value of 40 optical units (ou). In a particularly preferred embodiment, these 24 hues are provided at three additional translucencies, 20 ou, 60 ou, and 80 ou. Combining the same hue in different translucencies yields a material which has a translucency in-between the original and which can be computed linearly, e.g. 50% 20 ou and 50% 40 ou=30 ou.

Preferably, value modifiers at each translucency level are further provided so that the value of the particular shade may be increased or decreased without affecting the translucency, hue, or chroma.

Additional hue modifiers are further provided in the event a shade is not between two hue angles, e.g. to the right of the bottom most angle or to the left of the top-most angle. Respectively, these shades would need to be more red and more yellow. Pink and yellow modifiers in each translucency level are further provided so that the hue can be manipulated without affecting translucency or value. This preferred, complete system would include the following porcelain powders listed in Table 1:

value. Preferred quantities for the yellow, red, grey value and white value modifiers are set forth in Table 2:

TABLE 2

|                     | L     | a     | b     | C    | h     |
|---------------------|-------|-------|-------|------|-------|
| Yellow Modifier     | 63.6  | −3.88 | 14.49 | 15.0 | 105.0 |
| Red Modifier        | 59.9  | 12.97 | 0.90  | 13.0 | 4.0   |
| Grey Value Modifier | 39.88 | 0.04  | −0.94 | 0.94 | 272.2 |
| White Value Modifier| 68.23 | −1.02 | 0.51  | 1.14 | 153.4 |

This system allows total flexibility in altering one color component without affecting the other three. Such a system provides an effective color system for the construction of an entire crown.

Another embodiment of the system in accordance with the present invention includes the components listed in Table 3 below.

TABLE 3

| Color System Component | Total Units |
|---|---|
| 25 Hue/Chroma Shades where L = 60 at 40 ou translucency | 25 |
| 1 Super Clear Incisal | 1 |
| 1 Clear Incisal | 1 |
| 1 Translucency Modifier to increase translucency, low value L = 20 | 1 |
| 1 Translucency Modifier to increase translucency, high value L = 80 | 1 |
| 1 Yellow Modifier to shift hue towards yellow at 40 ou translucency | 1 |
| 1 Pink Modifier to shift hue towards pink at 40 ou translucency | 1 |
| 1 Gray Modifier to increase value at 40 ou translucency | 1 |
| TOTAL UNITS OF PORCELAIN POWDER | 32 |

TABLE 1

| Color System Component | Total Units |
|---|---|
| 25 Opaque porcelains for covering a metal surface | 25 |
| 25 Margin porcelains | 25 |
| 25 Hue/Chroma Shades where L = 60 at 20 ou | 25 |
| 25 Hue/Chroma Shades where L = 60 at 40 ou | 25 |
| 25 Hue/Chroma Shades where L = 60 at 60 ou | 25 |
| 25 Hue/Chroma Shades where L = 60 at 80 ou | 24 |
| 1 Super Clear Incisal | 1 |
| 1 Clear Incisal | 1 |
| 1 Value Modifier to lower value (gray), one each at translucency levels 20, 40, 60, 80 | 4 |
| 1 Value Modifier to increase value (white), one each at translucency levels 20, 40, 60, 80 | 4 |
| 1 Yellow Modifier to shift hue towards yellow, one each at translucency levels 20, 40, 60, 80 | 4 |
| 1 Red Modifier to shift hue towards pink at translucency levels 20, 40, 60, 80 | 4 |
| 4 Chroma Modifiers to increase chroma at translucency levels 20, 40, 60, 80 | 4 |
| TOTAL UNITS OF PORCELAIN POWDERS | 171 |

Preferably, the range of value, hue, chroma and translucency parameters of this and subsequently-described embodiments are selected so as to represent the teeth of 95% or more of the human population. Value will accordingly be in the range from about 50 to about 80. For the hue/chroma shades, hue is preferably in the range from about 79 to about 98, and chroma is the range from about 13 to about 28. As disclosed in U.S. Pat. No. 5,498,157 to Hall, the central color for a given hue/chroma subset at adjacent values is offset in the range of 2–4 degrees, and more preferably about 3 degrees of hue toward red for each 4–6 unit decrease in This system allows modification of hue, chroma, and value, but certain modifications would also affect translucency. Translucency is also modifiable, but such modification would affect chroma and value. This color system may be desirable where control of translucence is not as important.

Still another embodiment of the present invention includes the components listed in the Table 4 below.

TABLE 4

| Color System Component | Total Units |
| --- | --- |
| 1 Translucency Modifier to increase translucency, low value L = 20 | 1 |
| 1 Translucency Modifier to increase translucency, high value L = 80 | 1 |
| 1 Yellow Modifier to shift hue towards yellow at 40 ou translucency | 1 |
| 1 Pink Modifier to shift hue towards pink at 40 ou translucency | 1 |
| 1 Gray Modifier to increase value at 40 ou translucency | 1 |
| TOTAL UNITS OF PORCELAIN POWDER | 5 |

This system offers a dentist or technician the ability to make their own custom shades and requires a minimal purchase of materials.

An alternative approach to the porcelain color systems of the present invention take advantage of the ability of a spectrophotometer to accurately measure color and provide a recipe for that color. The present practice of providing a variety of Hue/Chroma shades is an artifact of color-matching by hand. Prior art color matching required color comparisons to be made by the practitioner, by manually comparing a tooth with a color sample. Numerous color samples were required, as it is quite difficult to estimate the quantities of porcelain colors which would accurately provide a shade falling in between two samples. Such multiplicity of shades is no longer required if a spectrophotometer is used to document a tooth's color, especially where the color data is transformed, via the appropriate algorithm, to a recipe for providing those colors. In this instance, a single shade of low hue and chroma can proved the "base" color, and the dentist or technician adds the appropriate quantities of red and yellow modifier. Preferably, the low hue and low chroma values correspond to the lowest values found in the teeth of 95% or more of the human population. The red and yellow modifiers are preferably provided in weighable form, that is, together with a filler material that allows accurate weighing of the red and yellow modifiers by the average dentist or laboratory. In accordance with this embodiment, the most complete system comprises the components shown in Table 5.

TABLE 5

| Color System Component | Total Units |
| --- | --- |
| 1 Opaque porcelain for covering a metal surface | 1 |
| 1 Margin porcelain | 1 |
| 1 Low Hue/Chroma Shades where L = 60 at 20 ou | 1 |
| 1 Low Hue/Chroma Shades where L = 60 at 40 ou | 1 |
| 1 Low Hue/Chroma Shades where L = 60 at 60 ou | 1 |
| 1 Low Hue/Chroma Shades where L = 60 at 80 ou | 1 |
| 1 Super Clear Incisal | 1 |
| 1 Clear Incisal | 1 |
| 1 Value Modifier to lower value, one each at translucency levels 20, 40, 60, 80 | 4 |
| 1 Value Modifier to increase value, one ea at translucency levels 20, 40, 60, 80 | 4 |
| 1 Yellow Modifier to shift hue towards yellow, one each at translucency levels 20, 40, 60, 80 | 4 |
| 1 Pink Modifier to shift hue towards pink at translucency levels 20, 40, 60, 80 | 4 |
| 4 Chroma Modifiers to increase chroma at translucency levels 20, 40, 60, 80 | 4 |
| TOTAL UNITS OF PORCELAIN POWDERS | 36 |

A more minimal set of porcelains would comprise the following components, yet still allow ease and maximum flexibility in the manufacture of a wide variety of tooth colors. Of course, other combinations of porcelains are possible, based on individual preference, convenience, cost, and other factors.

| | |
| --- | --- |
| 1 Opaque porcelain for covering a metal surface | 1 |
| 1 Margin porcelain | 1 |
| 1 Low Hue/Chroma Shades where L = 60 at 40 ou translucency | 1 |
| 1 Super Clear Incisal | 1 |
| 1 Clear Incisal | 1 |
| 1 Value Modifier to lower value at 20 ou translucency | 1 |
| 1 Value Modifier to increase value at 80 ou translucency | 1 |
| 1 Yellow Modifier to shift hue towards yellow, at translucency level 40 | 1 |
| 1 Pink Modifier to shift hue towards pink at translucency level 40 | 1 |
| 1 Chroma Modifiers to increase chroma at translucency levels 40 | 1 |
| TOTAL UNITS OF PORCELAIN POWDERS | 10 |

In a preferred embodiment, a spectrophotometer supplies the color parameters, and in a particularly preferred embodiment, formulations for each color are provided to the dentist or technician based on these color parameters. Suitable devices for measuring appropriate amounts of porcelain powder include those known in the arts such as a metering device comprising an auger/feed screw (made out of alumina or plastic to prevent metal contamination of the powder) with fine threads to accurately deliver the corresponding amount of powder. Preferably, an automated system is connected to the spectrophotometer and automated for a given batch size. Alternatively, the porcelain powder can be supplied in small tablets or pill form with the provided formulation including how many units of each material are to be used. These materials could then be combined and crushed into a powder by a suitable crushing method, e.g. using a mortar and pestle, to yield the desired shade.

Manufacture of porcelains having the above-identified color characteristics is known in the art, and described, for example, in U.S. Pat. No. 4,828,117 to Panzera et al., which is herein incorporated by reference in its entirety.

The following example is merely provided for illustrative purposes and is not intended to limit the broad scope of the present invention.

EXAMPLE 1

The following process can be used to make a porcelain dental restoration.

1. Illuminate a reference object with a Pikkio spectrophotometer by contacting the probe head of a spectrophotometer with the reference object. Gathering reflected light from the first spot, having a diameter of 1 mm, sending the gathered light to a spectrometer where it is converted into its spectral components and converted into first analog signals. Digitizing and storing the first analog signals 2. Illuminate a second, and optionally a third, spot each having a diameter of 1 mm on the reference object and gathering second reflected light, sending the second gathered light to a spectrometer where it is converted into its spectral components and converted into second analog signals, digitizing and storing the second analog signals.

3. Obtain an analog signal for a tooth abutting the area designated for the dental restoration in the same manner as described in steps 1 and 2.

4. Obtain an ambient reading adjustment by contacting the abutting tooth with the probe head, gathering light reflected from the tooth, without illuminating the tooth, sending the gathered light to a spectrometer where it is converted into its spectral components and ambient analog signals, digitizing and storing the ambient analog signals;

5. Correct the data for ambient influence, varying luminance and light loss due to transparency by subtracting the influence of the ambient light from the measure values of the abutting tooth, dividing that value by the reference values, and finally adding the correction corresponding to the light loss due to translucency to obtain remission data.

6. Correct the remission data by multiplying the remission data with the remission data of the reference object, and using the corrected remission data to determine the color component values. In this case the color component values were: R2 (see FIG. 2), hue 88, chroma 16, value 60, and translucency 40 ou, for example.

EXAMPLE 2

By way of example, R1 & R3 (FIG. 2) are as follows, wherein three shaded porcelains were batched according to the following formulations by weight percent (wt. %):

| Component | R1 | R3 | T3 |
| --- | --- | --- | --- |
| Unshaded Feldspathic Porcelain | 99.5612 | 99.2300 | 99.2668 |
| Yellow Pigment | 0.1126 | 0.2393 | 0.1976 |
| Pink Pigment | 0.2724 | 0.4386 | 0.5017 |
| Grey Pigment | 0.0538 | 0.0891 | 0.0339 |
| Total | 100.0000 | 100.0000 | 100.0000 |

The pigments used in the above formulations can be characterized by their color parameters in certain concentrations. The color parameters for each pigment mixed with the same unshaded feldspathic porcelain in given concentrations are as follows:

| Parameter | Unshaded Porcelain | Yellow Pigment | Pink Pigment | Grey Pigment |
| --- | --- | --- | --- | --- |
| Pigment Concentration | — | 0.5% | 0.5% | 0.3% |
| L | 61.15 | 64.96 | 60.25 | 51.90 |
| a | −0.92 | −5.41 | 8.00 | −0.59 |
| b | 0.66 | 37.51 | 0.42 | −0.83 |
| C | 1.13 | 37.90 | 8.01 | 1.02 |
| h | 144.37 | 98.21 | 3.02 | 234.60 |

Each of the shaded porcelains were blended separately to result in a homogeneous mix. Dry-pressed disks were made from each powder and fired according to the manufacturer's recommended firing schedule. Each disk was made from 2.5 g of powder and was approximately 19 mm in diameter and 3.7 mm thick after firing.

The color parameters of each disk were measured using a Spectro/plus™ spectrophotometer manufactured by Tecnidyne (also sold as the ColorTec-SCM) and Colorsoft software by ColorTec. The color parameters were read in reference to D65/10° illuminations standard.

The following is a summary of the resulting color parameters for each shaded disk.

| | R1 | | | R3 | | | T3 | | |
| --- | --- | --- | --- | --- | --- | --- | --- | --- | --- |
| Parameter | Meas. | Target | ΔE | Meas. | Target | ΔE | Meas. | Target | ΔE |
| L | 60.96 | 60 | 1.01 | 60.60 | 60 | 0.81 | 61.71 | 60 | 1.75 |
| a | 0.63 | 0.45 | | 0.89 | 0.66 | | 2.57 | 2.64 | |
| b | 12.71 | 12.99 | | 19.48 | 18.99 | | 18.45 | 18.82 | |
| C | 12.72 | 13 | | 19.50 | 19 | | 18.63 | 19 | |
| h | 87.18 | 88 | | 87.39 | 88 | | 82.07 | 82 | |

The target values shown above are as shown on FIG. 2. The measured values of the batch powders match the R1, R2, and T3 shades shown on FIG. 2.

EXAMPLE 3

To show that the shades are linear in nature and can be used to make shades that fall in between two shades of the shade system, intermediate shades were made from equal ixes of two shades.

Shade R1–R3 is made from equal parts of R1 and R3 (i.e. 50% shade R1 and 50% shade R3) and shows how chroma can be changed while maintaining a constant hue. In this case, the mixture should match the color parameters of R2 (L=60, a=0.54, b=15.99, C=16, h=88). The two shaded powders were mixed together in equal parts to form a homogeneous mixture. Drypressed disks were prepared in the same manner as for the individual shaded powders. The color parameters of the fired disk was then read on the same spectrophotometer:

| | R1 measured | R3 measured | Target R1–R3 50/50 mix | Measured R1–R3 50/50 mix |
| --- | --- | --- | --- | --- |
| L | 60.096 | 60.60 | 60 | 60.63 |
| a | 0.63 | 0.89 | 0.54 | 0.69 |

-continued

|   | R1 measured | R3 measured | Target R1–R3 50/50 mix | Measured R1–R3 50/50 mix |
|---|---|---|---|---|
| b | 12.71 | 19.48 | 15.99 | 16.53 |
| C | 12.72 | 19.50 | 16 | 16.55 |
| h | 87.18 | 87.39 | 88 | 87.60 |

ΔE = 0.84

Shade R3–T3 is made from equal parts of R3 and T3 (i.e. 50% shade R3 and 50% shade U3) and shows how hue can be changed while maintaining a constant chroma. The two shaded powders were mixed together in equal parts to form a homogeneous mixture. Drypressed disks were prepared in the same manner as for the individual shaded powders. The color parameters of the fired disk was then read on the same spectrophotometer.

|   | R3 measured | T3 measured | Target R3–T3 50/50 mix | Measured R1–R3 50/50 mix |
|---|---|---|---|---|
| L | 60.60 | 61.71 | 60 | 60.46 |
| a | 0.89 | 2.57 | 1.66 | 1.77 |
| b | 19.48 | 18.45 | 18.93 | 18.96 |
| C | 19.50 | 18.63 | 19 | 19.04 |
| h | 87.39 | 82.07 | 85 | 84.66 |

ΔE = 0.47

EXAMPLE 4

In addition to mixing two premixed shaded powders, modifiers can be used to change hue/chroma. The modifiers are comprised of a single pigment mixed with the unshaded feldspathic porcelain powder. These modifiers can then be used to change the hue and/or chroma or a premixed shaded powder.

Yellow and Red modifiers were made using 0.1% yellow pigment in unshaded powder and 1.0% pink pigment in unshaded powder. The resulting color parameters for these modifiers are as follows:

| Parameter | Yellow Modifier | Red Modifier |
|---|---|---|
| L | 63.56 | 59.92 |
| a | −4.08 | 12.55 |
| b | 14.83 | 0.86 |
| C | 15.38 | 12.58 |
| h | 105.39 | 3.92 |

Equal parts of R1 and Yellow Modifier were mixed together to form a homogeneous mixture. Equal parts of T3 and Red Modifier were mixed together to form a homogeneous mixture. Dry-pressed parameters of the fired disk was then read on the above spectrophotometer:

| Parameter | R1 + Modifier | T3 + Red Modifier |
|---|---|---|
| L | 60.90 | 60.80 |
| a | −1.14 | 6.82 |
| b | 13.47 | 11.05 |
| C | 13.52 | 12.99 |
| h | 94.83 | 58.31 |

Figure 4:
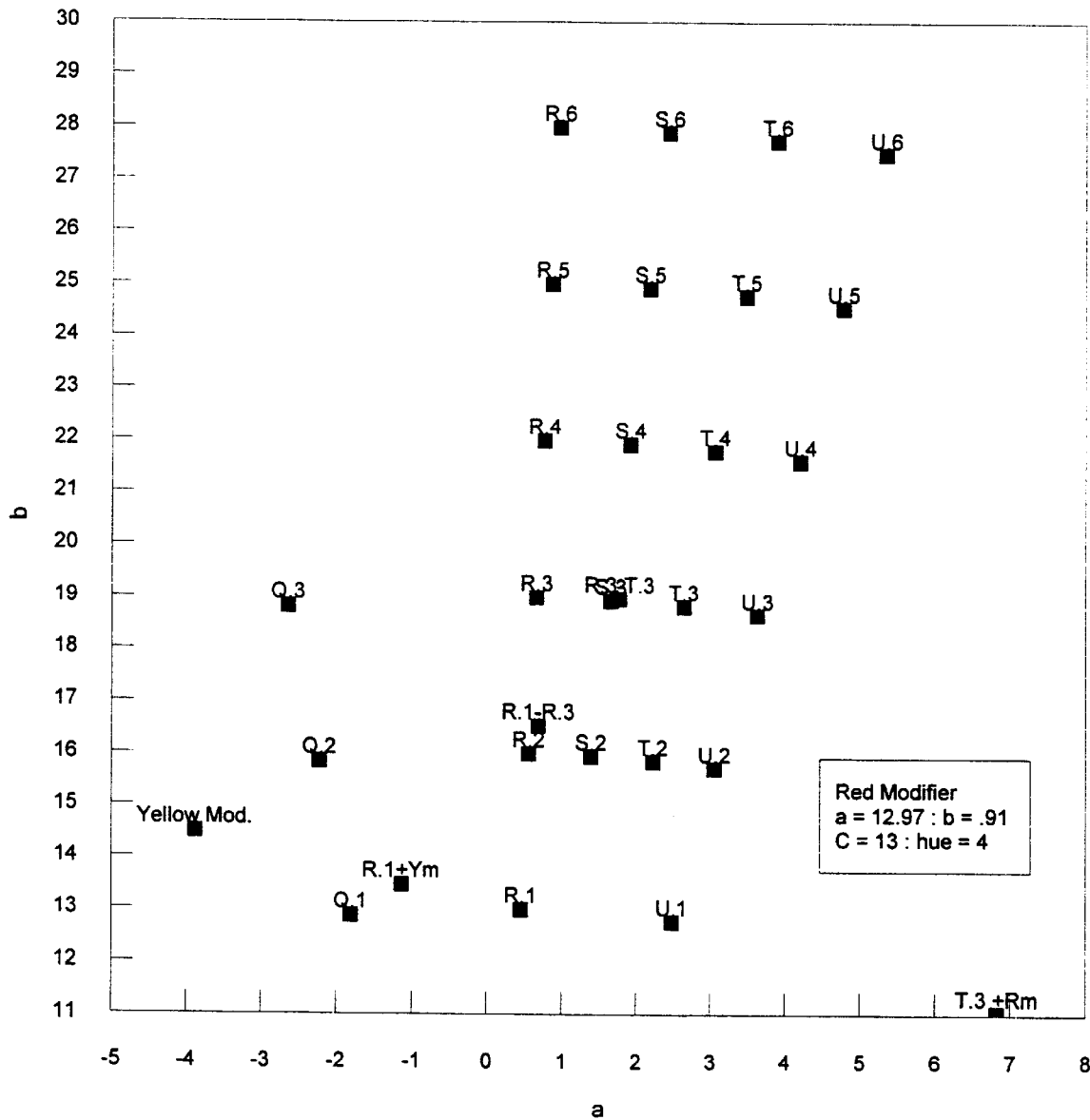
FIG. 4 is a graph showing another embodiment of the shades of present invention and examples.

These modified shades are plotted along with the compolete pre-mixed shade system in FIG. 4.

In accordance with the present invention, the color system may be applied to other dental restorative materials besides porcelain/ceramic materials, including composite resins that are used directly by a dentist or those used indirectly by a laboratory. For example, suitable composite resins are available under the trade names Sculpture and FibreKor, both commercially available from Jeneric/Pentron Inc., Wallingford, Conn. Such resins may be supplied to the practitioner packaged in a syringe with an identifying color associated therewith.

It will be understood that a person skilled in the art may make modification to the preferred embodiments shown herewith within the scope and intent of the claims. While the present invention has been described as carried out in a specific embodiment thereof, it is not intended to be limited thereby but is intended to cover the invention broadly within the scope and spirit of the claims.

What is claimed is:

1. A color system for porcelain dental restorations, comprising:
    a set of powders comprising a plurality of powders, wherein individual powders have a color component difference which is equidistant for hue, chroma, and value when plotted on a polar co-ordinate graph of color space, and wherein at least two of said powders can be utilized to adjust a single color component of hue, chroma, value, or translucency, without affecting another of said color components.

2. A color system for porcelain dental restorations as in claim 1, further comprising
    a plurality of subsets of powders having:
    different translucency and constant hue, chroma and value between the subsets with consecutive subsets having substantially equivalent delta translucency optical units; wherein
    within each subset of constant translucency, the powders have constant value and varying hue and chroma such that consecutive powders have substantially equivalent delta chroma and delta hue.

3. A color system for porcelain dental restorations as in claim 2, further comprising at least one value modifier powder.

4. A color system for porcelain dental restorations as in claim 3, wherein said value modifier powder includes a modifier to lower value and a modifier to increase value.

5. A color system for porcelain dental restorations as in claim 2, further comprising at least one hue modifier powder capable of shifting hue towards yellow or pink.

6. A color system for porcelain dental restorations as in claim 5, further comprising at least one yellow hue modifier powder capable of shifting hue towards yellow and at least one pink hue modifier powder capable of shifting hue towards pink.

7. A color system for porcelain dental restorations as in claim 6, further comprising a yellow hue modifier powder for each subset, said yellow hue modifier powder having a translucency equivalent to the respective subset translucency, and a pink hue modifier powder for each subset, said pink hue modifier powder having a translucency equivalent to the respective subset translucency.

8. A color system for porcelain dental restorations as in claim 2, further comprising at least one of a clear incisal powder, a chroma modifier powder, or a combination thereof.

9. A color system for porcelain dental restorations as in claim 2, further comprising a chroma modifier powder for each subset, said chroma modifier powder having a translucency equivalent to the respective subset translucency.

10. A color system for porcelain dental restorations as in claim 2, further comprising at least one value modifier powder, at least one hue modifier powder, and at least one chroma modifier powder.

11. A color system for porcelain dental restorations as in claim 2, wherein at least one hue and chroma value are identical to a hue and chroma value of an adjacent subset.

12. A color system for porcelain dental restorations as in claim 2, wherein the hue is in the range from about 79 to about 98, and the chroma is in the range from about 13 to about 28.

13. A porcelain dental restoration formed with the color system of claim 2.

14. A color system for porcelain dental restorations as in claim 1, further comprising a plurality of a first subset of powders having different translucency and constant hue, chroma and value between the subsets with consecutive subsets having substantially equivalent delta translucency optical units; wherein within each subset the hue and chroma of each powder correspond to the lowest hue and the lowest chroma found in the teeth of 95% or more of the human population; and a second subset of colors comprising a red modifier and a yellow modifier.

15. A color system for porcelain dental restorations as in claim 13, further comprising at least one value modifier powder.

16. A color system for porcelain dental restorations as in claim 15, wherein said at least one value modifier powder includes a modifier to lower value and a modifier to increase value.

17. A color system for porcelain dental restorations as in claim 15, wherein said at least one value modifier powder is at the same translucency level as at least one of the first subset of powders.

18. A porcelain dental restoration formed with the color system of claim 14.

19. A porcelain dental restoration formed with the color system of claim 1.

20. A color system for porcelain dental restorations, comprising:

a set of powders comprising a plurality of powders, wherein at least one powder has approximately the lowest combination of hue and chroma found in greater than 95% of human teeth at a first translucency level; and a second subset of colors comprising a red modifier and a yellow modifier.

21. A color system for porcelain dental restorations as in claim 20, further comprising at least one value modifier powder.

22. A porcelain dental restoration formed with the color system of claim 20.

23. A method for forming a powder to be used in making a dental restoration, comprising:

a. using a spectrophotometer to determine a desired color having the color components of translucency, hue, value, and chroma;

b. choosing, among a set of powders comprising a plurality of powders, wherein individual powders are equidistant in a polar co-ordinate color space, and wherein two of said powders can be utilized to adjust a single color component, hue, chroma, value, or translucency, without affecting another of said color components, the powders which have the closest color components to said desired color components, wherein at least one of said powders has one color component value greater than said desired color component value and another of said powders has the same color component value less than said desired color component value; and c. combining two of said chosen powders at an appropriate ratio to obtain a combined powder having said desired color component values.

24. A method for forming a powder to be used in making a dental restoration as in claim 23, further comprising repeating steps "b" and "c" for each color component which is not substantially equivalent to said desired color component values, wherein each color component is adjusted independently of other color components.

25. A method for preparing a powder to be used in making a dental restoration as in claim 23, further comprising:

illuminating a tooth with light;

recording the light reflected from the tooth; and converting the recorded light into desired color component values.

* * * * *

UNITED STATES PATENT AND TRADEMARK OFFICE
CERTIFICATE OF CORRECTION

PATENT NO.    : 6,030,209
DATED         : February 29, 2000
INVENTOR(S)   : Carlino Panzera et al.

Figure 1:
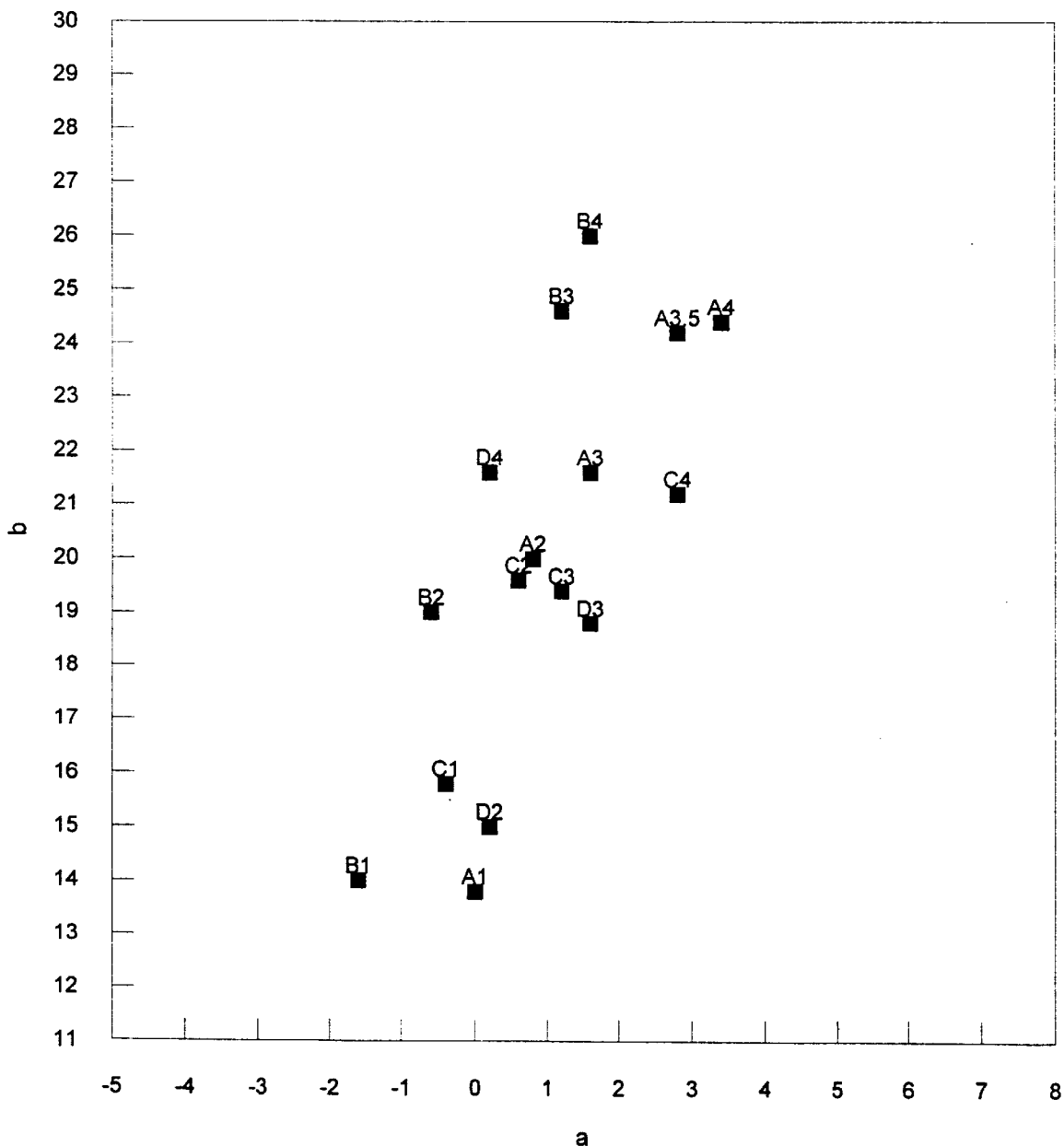
FIG. 1 is a graph showing the distribution of the shades in color space of the prior art Vita Lumen® shade guide system manufactured by Vita Zahnfabrik.

It is certified that error appears in the above-identified patent and that said Letters Patent is hereby corrected as shown below:

Drawings,
Substitute Figure 1 whereby it has been labeled "Prior Art" as shown below:

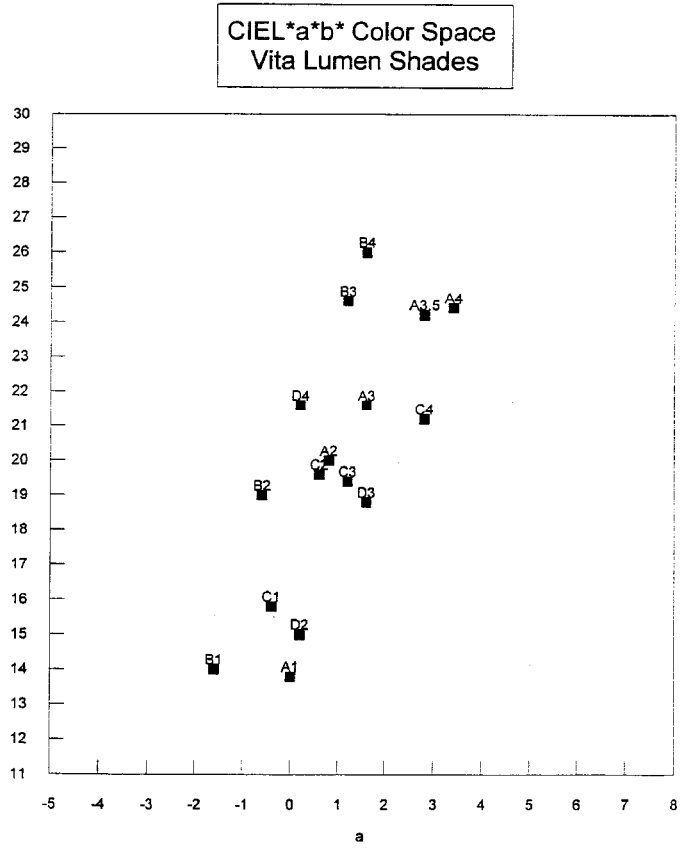

FIG. I
PRIOR ART

Column 2,
Line 7, after "tan$^{-1}$(b*/a*)" insert -- . --
Line 8, after "as" delete "(|a*$^2$+b*$^2$|)$^{½}$" and insert therefor -- ([a*$^2$+b*$^2$])$^{½}$ --
Line 12, after "lightness" delete "if" and insert therefor -- is --

Column 6,
Line 62, after "Thus" delete "calorimetric" and insert therefor -- colorimetric --

UNITED STATES PATENT AND TRADEMARK OFFICE
CERTIFICATE OF CORRECTION

PATENT NO.    : 6,030,209
DATED         : February 29, 2000
INVENTOR(S)   : Carlino Panzera et al.

It is certified that error appears in the above-identified patent and that said Letters Patent is hereby corrected as shown below:

<u>Column 8,</u>
Line 2, after "and" delete "seconds" and insert therefor -- second --
Line 35, after "thereafter," insert -- be --
Line 41, after "composition" delete "with" and insert therefor -- which --
Line 43, after "apparatus" delete "of" and insert therefor -- or --

<u>Column 11,</u>
Line 35, after "can" delete "proved" and insert therefor -- provide --

<u>Column 14,</u>
Line 56, before "of" delete "ixes" and insert therefor -- mixes --

<u>Column 16,</u>
Line 11, after "the" delete "compolete" and insert therefor -- complete --

<u>Column 17,</u>
Line 40, after "claim" delete "13" and insert therefor -- 14 --

Signed and Sealed this

Twenty-fourth Day of February, 2004

JON W. DUDAS
*Acting Director of the United States Patent and Trademark Office*